US008313919B2

(12) United States Patent
Uttenthal et al.

(10) Patent No.: US 8,313,919 B2
(45) Date of Patent: Nov. 20, 2012

(54) DIAGNOSTIC TEST FOR RENAL INJURY

(75) Inventors: Lars Otto Uttenthal, Salamanca (ES); Kristian Bangert, Holte (DK)

(73) Assignee: BioPorto Diagnostics A/S, Gentofte (DK)

( * ) Notice: Subject to any disclaimer, the term of this patent is extended or adjusted under 35 U.S.C. 154(b) by 317 days.

(21) Appl. No.: 12/531,986

(22) PCT Filed: Mar. 18, 2008

(86) PCT No.: PCT/DK2008/050069
§ 371 (c)(1),
(2), (4) Date: Oct. 5, 2009

(87) PCT Pub. No.: WO2008/113363
PCT Pub. Date: Sep. 25, 2008

(65) Prior Publication Data
US 2010/0035364 A1 Feb. 11, 2010

Related U.S. Application Data

(60) Provisional application No. 60/919,277, filed on Mar. 21, 2007.

(51) Int. Cl.
C12Q 1/37 (2006.01)
G01N 33/53 (2006.01)
G01N 33/573 (2006.01)
G01N 33/50 (2006.01)
G01N 33/493 (2006.01)

(52) U.S. Cl. .............. 435/23; 435/7.1; 435/7.4; 436/86

(58) Field of Classification Search .................. None
See application file for complete search history.

(56) References Cited

U.S. PATENT DOCUMENTS

| | | |
|---|---|---|
| 3,635,091 A | 1/1972 | Linzer |
| 4,302,471 A | 11/1981 | Casagrande et al. |
| 4,357,343 A | 11/1982 | Madsen et al. |
| 4,376,110 A | 3/1983 | David et al. |
| 4,640,909 A | 2/1987 | Ramsden et al. |
| 5,273,961 A | 12/1993 | Clark |
| 5,405,832 A | 4/1995 | Potempa |
| 5,527,714 A | 6/1996 | Kosako |
| 5,552,313 A | 9/1996 | Calvet et al. |
| 5,627,034 A | 5/1997 | Gould et al. |
| 5,750,345 A | 5/1998 | Bowie |
| 5,939,272 A | 8/1999 | Buechler et al. |
| 6,136,526 A | 10/2000 | Venge |
| 6,143,720 A | 11/2000 | Conklin |
| 6,309,888 B1 | 10/2001 | Holvoet et al. |
| 6,447,989 B1 | 9/2002 | Comper |
| 6,537,802 B1 | 3/2003 | Alocilja et al. |
| 6,664,385 B1 | 12/2003 | Sanicola-Nadel et al. |
| 6,762,032 B1 | 7/2004 | Nelson et al. |
| 6,847,451 B2 | 1/2005 | Pugh |
| 6,986,995 B2 | 1/2006 | Rose et al. |
| 7,056,702 B2 | 6/2006 | Villanueva et al. |
| 7,153,660 B2 | 12/2006 | Moses et al. |
| 7,252,998 B2 | 8/2007 | Skerra et al. |
| 2002/0048779 A1 | 4/2002 | Brady et al. |
| 2002/0110799 A1 | 8/2002 | Comper |
| 2003/0109420 A1 | 6/2003 | Valkirs et al. |
| 2003/0119209 A1 | 6/2003 | Kaylor et al. |
| 2003/0175686 A1 | 9/2003 | Rose et al. |
| 2004/0121343 A1 | 6/2004 | Buechler et al. |
| 2004/0203083 A1 | 10/2004 | Buechler et al. |
| 2004/0219603 A1 | 11/2004 | Devarajan et al. |
| 2005/0261191 A1 | 11/2005 | Barasch et al. |
| 2005/0272101 A1 | 12/2005 | Devarajan et al. |
| 2006/0008804 A1 | 1/2006 | Chibout et al. |
| 2007/0037232 A1 | 2/2007 | Barasch et al. |
| 2007/0196876 A1 | 8/2007 | Moses et al. |
| 2007/0254370 A1 | 11/2007 | Devarajan et al. |
| 2008/0014604 A1 | 1/2008 | Devarajan et al. |
| 2008/0014644 A1 | 1/2008 | Barasch et al. |
| 2008/0090304 A1 | 4/2008 | Barasch et al. |
| 2009/0123941 A1 | 5/2009 | Devarajan et al. |
| 2009/0123946 A1 | 5/2009 | Birkenmeyer et al. |
| 2009/0123970 A1 | 5/2009 | Tu et al. |
| 2009/0124022 A1 | 5/2009 | Birkenmeyer et al. |
| 2009/0142774 A1 | 6/2009 | Devarajan et al. |
| 2009/0170143 A1 | 7/2009 | Uttenthal et al. |
| 2009/0181407 A1 | 7/2009 | Devarajan et al. |
| 2010/0015648 A1 | 1/2010 | Barasch et al. |

FOREIGN PATENT DOCUMENTS

| | | |
|---|---|---|
| EP | 1925677 | 5/2008 |
| WO | WO 95/29404 | 11/1995 |
| WO | WO 96/32647 | 10/1996 |
| WO | WO 03/029462 | 4/2003 |
| WO | WO 03/029463 | 4/2003 |
| WO | WO 2004/005544 | 1/2004 |
| WO | WO 2004/088276 | 10/2004 |

(Continued)

OTHER PUBLICATIONS

Griffith et al. "Acute reversible intrinsic renal failure" Surg Gynecol Obstet. Apr. 1978;146(4):631-40.*

Aulitzky et al. 1992. Measurement of Urinary Clusterin as an Index of Nephrotoxicity. P.S.E.B.M., vol. 199, pp. 93-96.

Bangert et al. 2006. NGAL is significantly increased in urine and plasma in acute renal failure. Intensive Care Medicine, Spinger Verlag, BE, p. S10, XP009091902, 19th ESICM Annual Congress, Barcelona, Spain.

Bangert K. et al. 2007. NGAL as a marker for renal injury in sepsis. Inflammation Research, Birkhauser Verlag, Basel, CH, pp. 104-105, XP008082913.

Bolignano et al. 2007. Neutrophil Gelatinase-Associated Lipocalin in Patients with Autosomal-DominantPolycystic Kidney Disease. Am J Nephrol;27:373-378.

Bolignano et al. 2007. Urinary Neutrophil Gelatinase-Associated Lipocalin (NGAL) is associated with severity of renal disease in proteinuric patients. Nephrol Dial Transplant, Nephrol Dial Transplant (2007), pp. 1-2.

(Continued)

Primary Examiner — Christine Foster
(74) Attorney, Agent, or Firm — Clark & Elbing LLP; Kristina Bieker-Brady

(57) ABSTRACT

A method is provided of diagnosing and monitoring acute renal injury leading to acute renal failure in a human or mammalian subject by determining the ratio of the concentration of neutrophil gelatinase-associated lipocalin (NGAL) in urine to that in plasma or serum.

20 Claims, 5 Drawing Sheets

FOREIGN PATENT DOCUMENTS

| WO | WO 2005/107793 | 11/2005 |
|----|----------------|---------|
| WO | WO 2005/121788 | 12/2005 |
| WO | WO 2006/066587 | 6/2006 |
| WO | WO 2007/044994 | 4/2007 |
| WO | WO 2007098102 | 8/2007 |
| WO | WO-2008/061149 | 5/2008 |
| WO | WO 2009/052390 | 4/2009 |
| WO | WO 2009/052392 | 4/2009 |
| WO | WO 2009/052400 | 4/2009 |
| WO | WO 2009/059259 | 5/2009 |
| WO | WO 2010/058378 | 5/2010 |

OTHER PUBLICATIONS

Devarajan et al. 2004. NGAL: A novel early biomarker of renal injury following cardiac surgery. Slides, Cincinnati Children's Hospital Medical Center, University of Cincinatti, OH, Colombia University, NY, from proceedings in EP 1 831 699.

Devarajan et al. 2006. AACC Expert Access Program: Novel Diagnostic Markers of Aerly Acute Kidney Injury (AKI). AACC, Online Dec. 14, 2006, pp. 1-45.

Friedl et al. 1999. Neutrophil gelatinase-associated lipocalin in normal and neoplastic human tissues. Cell type-specific pattern of expression. The Histochemical Journal 31; 433-441.

Han et al. 2002. Kidney Injury Molecule-1 (KIM-1): A novel biomarker for human renal proximal tubule injury. Kidney International, vol. 62, pp. 237-244.

Kjeldsen et al. 1993. Isolation and Primary Structure of NGAL, a Novel Protein Associated with Human Neutrophil Gelatinase. The Journal of Biological Chemistry, vol. 268, No. 14, Issue May 15, pp. 10425-10432.

Kjeldsen et al. 1996. Characterization of two ELISAs for NGAL, a newly described lipocalin in human neutrophils. Journal of Immunological Methods, 198, pp. 155-164.

Kotanko et al. 2000. Urinary N-Acetyl-β-D-Glucosaminidase and Neopterin Aid in the Diagnosis of Rejection and Acute Tubular Necrosis in Initially Nonfunctioning Kidney Grafts. Nephron;84:228-235.

Liu et al. 1995. Identification of a New Acute Phase Protein. The Journal of Biological Chemistry, vol. 270, No. 38, issue Sep. 22, pp. 22565-22570.

Mishra J. et al. 2003. Identification of Neutrophil Gelatinase-Associated Lipocalin as a Novel Early Urinary Biomarker for Ischemic Renal Injury. Journal of the American Society of Nephrology, Williams and Wilkins, Baltimore, MD, US, vol. 14, No. 10, October, pp. 2534-2543, XP002377943.

Mishra J. et al. 2005. Neutrophil gelatinase-associated lipocalin (NGAL) as a biomarker for acute renal injury after cardiac surgery. Lancet The, Lancet Limited. London GB, pp. 1231-1238, XP004824250.

Monier et al. 2000. Gelatinase isoforms in urine from bladder cancer patients. Clinics Chimica Acta 299, 11-23.

Muramatsu et al. 2002. Early detection of cysteine rich protein 61 (CYR61, CCN1) in urine following renal ischemic reperfusion injury.Kidney International, vol. 62, pp. 1601-1610.

Nielsen et al. 1999. Rectal Dialysate and Fecal Concentrations of Neutrophil Gelatinase-Associated Lipocalin, Interleukin-8, and Tumor Necrosis Factor-alfa in Ulcerative Colitis. The American Journal of Gastroenterology 94(10); 1999, pp. 2923-2928.

Penders et al. 2004. Alpha 1-microglobulin: clinical laboratory aspects and applications. Clinica Chimica Acta 346 (2004) 107-118.

Stoesz and Gould. 1995. Overexpression of neu-related lipocalin (NRL) in neu-initiated but not ras or chemically initiated rat mammary carcinomas. Oncogene, 11, 2233-2241.

Triebel et al. 1992. A 25 kDa $\alpha_2$-microglobulin-related protein is a component of the 125 kDa form of human gelatinase. FEBS 11904, vol. 314, nummer 3, 386-388.

Tsuchida et al. 2004. Lipocalin-Type Prostaglandin D Synthase in Urine in Adriamycin-Induced Nephropathy of Mice. Nephron Physiol., 96: p. 42-51.

Xu et al. 1995. Serum measurements of human neutrophil lipocalin (HNL) discriminate between acute bacterial and viral infections. Scand J. Clin Lab Invest 1995; 55 125-131.

Xu et al. 2000. Lipocalins as biochemical markers of disease. Biochimica et Biophysica Acta 1482 298-307.

Yan et al. 2001. The High Molecular Weight Urinary Matrix Metalloproteinase (MMP) Activity Is a Complex of Gelatinase B/MMP-9 and Neutrophil Gelatinase-associated Lipocalin (NGAL). The Journal of Biological Chemistry, vol. 276, No. 40, pp. 37258-37265.

U.S. Appl. No. 11/096,113, filed Dec. 8, 2005, Devarajan et al.
U.S. Appl. No. 12/104,408, filed Apr. 16, 2008, Tu et al.
U.S. Appl. No. 60/458,143, filed Mar. 27, 2003, Devarajan et al.
U.S. Appl. No. 60/481,596, filed Nov. 4, 2007, Devarajan et al.
U.S. Appl. No. 60/577,662, filed Jun. 7, 2004, Devarajan et al.
U.S. Appl. No. 60/637,503, filed Dec. 20, 2004, Uttenthal et al.
U.S. Appl. No. 60/719,307, filed Sep. 21, 2005, Uttenthal et al.
U.S. Appl. No. 60/859,136, filed Nov. 14, 2006, Valkiers et al.
U.S. Appl. No. 60/981,470, filed Feb. 23, 2007, Libertyville et al.
U.S. Appl. No. 60/981,471, filed Oct. 19, 2007, Birkenmeyer et al.
U.S. Appl. No. 60/981,473, filed Oct. 19, 2007, Birkenmeyer et al.

Alessio et al. 1985. "Reliability of urinary creatinine as a parameter used to adjust values of urinary biological indicators" Int Arch Occup. Environ. Health 55: 99-106.

Allen RA, Erickson RW, Jesaitis AJ (1989): "Identification of a human neutrophil protein of Mr 24 000 that binds N-formyl peptides: co-sedimentation with specific granules". Biochim Biophys Acta 991:123-133.

Amin et al. "Identification of Putative Gene-Based Markers of Renal Toxicity" Environmental Health Perspectives; vol. 112; nr. 4; pp. 465-479; Mar. 2004.

Anonymous (2007) Product inlay of the Quantikine Human MMP-9/NGAL Complex Immunoassay kit, Catalog No. DM9L20, R&D Systems, Inc., Minneapolis, MN, USA.

Antibodyshop O14a Product Specification Anti-NGAL (human, neutrophil gelatinase-associated lipocalin) Mouse monoclonal antibody. Product No. HYB 211-01; Mar. 31, 2009.

Antibodyshop O14b Product Specification Anti-NGAL (human, neutrophil gelatinase-associated lipocalin) Mouse monoclonal antibody, biotinylated. Product No. HYB 211-01 B; Mar. 31, 2009.

Antibodyshop O14c Product Specification Anti-NGAL (human, neutrophil gelatinase-associated lipocalin) Mouse monoclonal antibody. Product No. HYB 211-02; Apr. 14, 2009.

Antibodyshop O14d Product Specification Anti-NGAL (human, neutrophil gelatinase-associated lipocalin) Mouse monoclonal antibody, biotinylated. Product No. HYB 211-02 B; Apr. 14, 2009.

Antibodyshop O14e Product Specification Anti-NGAL (human, neutrophil gelatinase-associated lipocalin) Mouse monoclonal antibody. Product No. HYB 211-05; Apr. 14, 2009.

Ashkenazi et al. 2006. "Precision of In-Hospital Triage in Mass-Casualty Incidents after Terror attacks" Prehospital Disaster Med., vol. 21, pp. 20-23.

Axelsson et al. 1995. "Studies of the release and turnover of a human neutrophil lipocalin". Scand J Clin Invest, 55: 577-588.

Bachorzewska-Gajewska et al. (2006): "Neutrophil-gelatinase-associated lipocalin and renal function after percutaneous coronary interventions"; Am J Nephrol, vol. 26, pp. 287-292.

Baker M (2005): "In biomarkers we trust?"; Nature Biotechnology, vol. 23, No. 3, pp. 297-304.

Balakumar et al. 2008. "Potential target sites to modulate vascular endothelial dysfunction: Current perspectives and future directions" Toxicology 245, 49-64.

Bangert et al. 2005. "Urinary NGAL is dramatically increased in acute renal failure". Abstract ESICM.

Barr et al. (2005): "Urinary creatinine concentrations in the U.S. population: Implications for urinary biologic monitoring measurements"; Environmental Health Perspectives 113: 192-200.

Bartsch et al. "Cloning and expression of human neutrophil lipocalin cDNA derived from bone marrow and ovarian cancer cells" FEBS Lett. 357:255-259, 1995.

Bast et al. "Translational Crossroads for Biomarkers" Clin Cancer Res 2005; 11(17), 6103-6108.

Bennett M et al (2008): "Urine NGAL predicts severity of acute kidney injury after cardiac surgery: A prospective study"; Clin J Am Soc Nephrol, vol. 3, pp. 665-673.

Bewick et al. 2004. "Statistics review 13: Receiver operating characteristic curves". Critical Care 8(6), 508-512.

Bläser et al. "A sandwich enzyme immunoassay for the determination of neutrophil lipocalin in body fluids". Clin Chim Acta 235 (1995); 137-145.
Bolignano D et al (2007): "Urinary neutrophil gelatinase-associated lipocalin (NGAL) is associated with severity of renal disease in proteinuric patients"; Nephrol Dial Transplant, vol. 23, No. 1, pp. 414-416.
Bolignano D et al (2010): "Neutrophil gelatinase-associated lipocalin (NGAL) in human neoplasias: A new protein enters the scene"; Cancer Letters, vol. 288, No. 1, pp. 10-16.
Bolignano et al. 2008: "Neutrophil gelatinase-associated lipocalin reflects the severity of renal impairment in subjects affected by chronic kidney disease"; Kidney Blood Press Res 31: 255-258.
Braunwald E et al (eds) (2002): Harrison's Manual of Medicine; McGraw-Hill Company; pp. 653.
Brenner & Rector (1986): The Kidney, 3rd edition, pp. 740-747.
Bu DX, Hemdahl AL, Gabrielsen A, Fuze J, Zhu C, Eriksson P, Yan ZQ (2006) "Induction of neutrophil gelatinase-associated lipocalin in vascular injury via activation of nuclear factor-kappaB". Am J Pathol 169:2245-2253.
Bundgaard et al. 1994. "Molecular cloning and expression of a cDNA encoding NGAL: a lipocalin expressed in human neutrophils". Biochem Biophys Res Commun; vol. 202(3):1468-75.
Carr MC et al (1994): "Urinary levels of the renal tubular enzyme N-acetyl-beta-D-glucosaminidase in unilateral obstructive uropathy"; The Journal of Urology; vol. 151, No. 2, pp. 442-445.
Chan et al. (1988): "The primary structure of rat alpha 2 mu globulin-related protein" Nucleic acid Res. vol. 16 No. 23, pp. 11368.
Chertow et al (1997): "Preoperative Renal Risk Stratification"; Circulation, vol. 95, nr. 4, pp. 878-884.
Christensen EI et al (2001): "Megalin and cubilin: synergistic endocytic receptors in renal proximal tubule"; Am J Physiol Renal Physiol, vol. 280, No. 4, pp. F562-F573.
CMS brochure; Feb. 2004: "Clinical Laboratory Improvement Amendments (CLIA)", Department of Health and Human Services, (two pages).
Cohen et al. 1993. "Induction of Type 2 Salivary Cystatin in Immunological and Chemical Kidney Injury" Critical Reviews in Oral Biology and Medicine, 4(3/4):553-563.
Costantini S et al (2002): "Pilot study on lipocalin expression into extracellular fluids of women in fertile age"; Minerva Ginecologica; vol. 54, No. 5, pp. 387-392.
Cowland et al. "Molecular Characterization and Pattern of Tissue Expression of the Gene for Neutrophil Gelatinase-Associated Lipocalin from Humans" Genomics 45: 17-23 1997.
Cruz DN et al (2009): "Plasma neutrophil gelatinase-associated lipocalin is an early biomarker for acute kidney injury in an adult ICU population"; Intensive Care Med, vol. 36, pp. 444-451, published online Dec. 3, 2009.
Dent et al. "Plasma neutrophil gelatinase-associated lipocalin predicts acute kidney injury, morbidity and mortality after pediatric cardiac surgery: a prospective uncontrolled cohort study" Crit Care 2007; 11(6):R127.
Devarajan. 2005. "Novel biomarkers for the early prediction of acute kidney injury". Cancer Therapy, vol. 3, 477-488.
Devireddy LR et al (2001): "Induction of Apoptosis by a Secreted Lipocalin That is Transcriptionally Regulated by IL-3 Deprivation"; Science, vol. 293, pp. 829-834.
Dharnidharka VR et al (2002): "Serum cystatin C is superior to serum creatinine as a marker of kidney function: a meta-analysis"; Am J Kidney Dis; vol. 40, nr. 2, pp. 221-226.
Dorland's illustrated medical dictionary, 29th Edition. W.B. Saunders Company, New York (2000); "cancer", "glomerulonephritis" and "neoplasm" pp. 273, 752, 1184-1185.
Dr. Devarajan's presentation entitled: "NGAL: A Novel Early Biomarker of Renal Injury Following Cardiac Surgery"; Oct. 2004, from opposition proceedings in EP 1 831 699.
Elneihoum et al. "Leukocyte activation detected by increased plasma levels inflammatory mediators in patients with ischemic cerebrovascular diseases". Stroke 27:1734-1738, 1996.
E-mail correspondence—Trine Overgaard Østerbye, Jaya Mishra and Claus Morsø Schrøder, 2004.
EP 1831699 Opp1 Abbott; Jul. 2, 2010, (32 pages).

EP 1831699 Opp2 Getica; Aug. 3, 2010. (25 pages).
EP 1831699 Opp3 Alere; Aug. 11, 2010, (61 pages).
EP 1831699 Opp4 Phadia; Aug. 11, 2010. (31 pages).
EP 1831699 Reply to oppositions filed; Dec. 23, 2010, (41 pages).
Exhibit A of Dr. Kunis' declaration: cover page of onsite program/meeting brochure of the American Society of Nephrology Renal Week 2004, Oct. 27-Nov. 1, 2004, St. Louis Missouri.
Exhibit B of Dr. Kunis' declaration: p. 334 and 335 of the onsite program of the American Society of Nephrology Renal Week 2004, Oct. 27-Nov. 1, 2004, St. Louis Missouri, indicating poster presentation S-PO204 of Oct. 31, 2004.
Exhibit C of Dr. Kunis' declaration: photograph of the poster of Kunis et al., American Society of Nephrology Renal Week 2004, Oct. 27-Nov. 1, 2004, St. Louis Missouri, "Ngal (neutrophil gelatinase-associated lipocalin) as a marker for tubular damage in patients with Acute Tubular Necrosis (ATM)" as presented during poster presentation SU-PO204.
Exhibit D of Dr. Kunis' declaration: clean copy reproduction/image file of the poster of Kunis et al., American Society of Nephrology Renal Week 2004, Oct. 27-Nov. 1, 2004, St. Louis Missouri, "Ngal (neutrophil gelatinase-associated lipocalin) as a marker for tubular damage in patients with Acute Tubular Necrosis (ATN)" as presented during poster presentation SU-PO204.
Flower DR et al (1991): "Mouse oncogene protein 24p3 is a member of the Lipocalin protein family"; Biochemical and Biophysical Research Communications, vol. 180, No. 1, pp. 69-74.
Forsblad et al. 2002. "Clinical manifestations of atherosclerosis in an elderly population are related to plasma neopterin, NGAL and endothelin-1, but not to Chlamydia pneumoniae serology". Int. Angiology 21(2) 173-9.
Fortescue EB et al (2000): "Predicting acute renal failure after coronary bypass surgery: cross-validation of two risk-stratification algorithms"; Kidney International; vol. 57, No. 6, pp. 2594-2602.
Fraser Chap 4 in Biological Variation: From Principles to Practice, AAAC Press, pp. 91-116, 2001.
Fukuda et al., Oct. 18, 2004: "Differential gene expression profiles of radioresistant oesophageal cancer cell lines established by continuous fractionated irradiation", British Journal of Cancer, vol. 91, No. 8, pp. 1543-1550.
Gale encyclopedia of medicine. "Definition of Blood plasma and serum in the Medical"; www.freedictionary.com; accessed on Nov. 30, 2010.
Gebhard et al., Mar. 3, 2000: "Is interleukin 6 an early marker of injury severity following major trauma in humans", Archives of Surgery, vol. 135, No. 3, pp. 291-295.
Grenier et al. "Evaluation of the Architect urine NGAL assay: Assay performance, specimen handling requirements and biological variability" Clin Biochem. Apr. 2010; 43-615-620.
Harbeson, A.E. 1936 "A case of turpentine poisoning" The Canadian Medical Association Journal, vol. 35, pp. 549-550.
Henderson's Dictionary of Biological Terms, 12th edition, Prentice Hall (2000); "Blood" and "Blood serum"; pp. 74-77, 576-577.
Herget-Rosenthal (2005): "One step forward in the early detection of acute renal failure"; Lancet, vol. 365, No. 9466, pp. 1205-1206.
Hraba-Renevey S et al. (1989): "SV40-induced expression of mouse gene 24p3 involves a post-transcriptional mechanism"; Oncogene, vol. 4, No. 5, pp. 601-608.
Hrubec TC et al (2002): "Plasma versus serum: specific differences in biochemical analyte values"; Journal of avian medicine and surgery; vol. 16, No. 2, pp. 101-105.
http://en.wikipedia.org/wiki/Diabetes_mellitus; "Diabetes Mellitus", Wikipedia, The Free Encyclopedia; accessed on Feb. 10, 2011, (15 pages).
Hvidberg V et al (2005): "The endocytic receptor megalin binds the iron transporting neutrophil-gelatinase-associated lipocalin with high affinity and mediates its cellular uptake"; FEBS Letters, vol. 579, No. 3, pp. 773-777.
Haase M et al (2009): "Novel biomarkers early predict the severity of acute kidney injury after cardiac surgery in adults"; The Annals of thoracic surgery, vol. 88, No. 1, pp. 124-130.

Haase-Fielitz A et al (2009): "Novel and conventional serum biomarkers predicting acute kidney injury in adult cardiac surgery—a prospective cohort study"; Critical Care Medicine; vol. 37, No. 2, pp. 553-560.

Haase-Fielitz A et al (2009): "The predictive performance of plasma neutrophil gelatinase-associated lipocalin (NGAL) increases with grade of acute kidney injury"; Nephrol Dial Transplant, vol. 24, No. 11, pp. 3349-3354.

Ichimura T et al (1998): "Kidney injury molecule-1 (KIM-1), a putative epithelial cell adhesion molecule containing a novel immunoglobulin domain, is up-regulated in renal cells after injury"; Journal of Biological Chemistry, vol. 273, No. 7, pp. 4135-4142.

Jones AP et al (1995): "Urinary N-acetyl-B-glucosaminidase activity in Type I diabetes mellitus"; Ann Clin Biochem; vol. 32, pp. 58-62.

Jönsson P et al (1999): "Extracorporeal circulation causes release of neutrophil gelatinase-associated lipocalin (NGAL)"; Mediators of Inflammation; vol. 8, No. 3, pp. 169-171.

Kjeldsen et al. "Isolation and Characterization of Gelatinase Granules From Human Neutrophils" Blood, vol. 83, No. 6 (Mar. 15, 1994): pp. 1640-1649.

Kjeldsen L et al (1993): "Structural and functional heterogeneity among peroxidase-negative granules in human neutrophils: identification of a distinct gelatinase-containing granule subset by combined immunocytochemistry and subcellular fractionation"; Blood, vol. 82, No. 10, pp. 3183-3191.

Kjeldsen L et al (1994): "Identification of neutrophil gelatinase-associated lipocalin as a novel matrix protein of specific granules in human neutrophils"; Blood, vol. 83, No. 3, pp. 799-807.

Kjeldsen L et al (2000): "Human neutrophil gelatinase-associated lipocalin and homologous proteins in rat and mouse"; Biochimica et Biophysica Acta, vol. 1482, No. 1-2, pp. 272-283.

Klausen P et al. 2005. "On mouse and man: neutrophil gelatinase associated lipocalin is not involved in apoptosis or acute response". European Journal of Haematology, 75:332-340.

Kunis declaration Oct. 31, 2004, part of Opposition proceedings against EP 1 831 699 B1 (5 pages).

Kunis et al., Poster abstract 3709 published on Oct. 31, 2004, American Society for Nephrology Renal Week.

LaBaer J (2005): "So, you want to look for biomarkers (introduction to the special biomarkers issue)"; Journal of Proteome Research, vol. 4, No. 4, pp. 1053-1059.

Lim R et al (2007): "Neutrophil gelatinase-associated lipocalin (NGAL) an early-screening biomarker for ovarian cancer: NGAL is associated with epidermal growth factor-induced epithelio-mesenchymal transition"; Int. J. Cancer; vol. 120, No. 11, pp. 2426-2434.

Matthaeus et al. (2001): "Co-regulation of neutrophil gelatinase-associated lipocalin and matrix metalloproteinase-9 in the post ischemic rat kidney"; J Am Soc Nephrol; 12:787A.

Matthaeus T et al (2001): "Acute Ischemic Renal Failure Induces Expression of Neutrophil Gelatinase-Associated Lipocalin and Matrix Metalloproteinase-9 in Damaged Tubuli"; Kidney and Blood Pressure Res., vol. 24, pp. 342 (Poster 268).

Mehta et al. 2007. "Acute kidney injury network: report of an initiative to improve outcomes in acute kidney injury". Critical Care 11(2), R31, (pp. 1-8).

Mishra et al. 2004. "Neutrophil gelatinase-associated lipocalin: A novel early urinary biomarker for cisplatin nephrotoxicity". Am. J Nephr, 24: 307-315 (Published online on May 12, 2004).

Molitoris BA (2003), "Transitioning to therapy in ischemic acute renal failure", J.Am.Soc. Neuphrol 14: pp. 265-267.

Mori et al. "Endocytic delivery of lipocalin-siderophore-iron complex rescues the kidney from ischemia-reperfusion injury" The Journal of Clinical Investigation; 115(3), 620-621, Mar. 2005—Enlarged and magnified version of Figure 1C, with logarithmic y-axis values and gridlines added.

Mori et al. 2005. "Endocytic delivery of lipocalin-siderophore-iron complex rescues the kidney from ischemia-reperfusion injury". The Journal of Clinical Investigation, vol. 115, No. 3, 610-621.

Mori K & Nakao K (2007):"Neutrophil gelatinase-associated lipocalin as the real-time indicator of active kidney damage"; Kidney International, vol. 71, pp. 967-970.

Moses et al. 1998. "Increased Incidence of Matrix Metalloproteinases in Urine of Cancer Patients". Cancer Research, vol. 58, 1395-1399.

Möller et al., Mar. 1998, "Cytokines and acute phase reactants during flare-up of contact allergy to gold", American Journal of Contact Dermatitis, vol. 9, No. 1, pp. 15-22.

Nickolas et al. 2008. "Sensitivity and Specificity of a Single Emergency Department Measurement of Urinary Neutrophil Gelatinase-Associated Lipocalin for Diagnosing Acute Kidney Injury". Annals of Internal Medicine, Jun. 3, 2008, vol. 148, No. 11, pp. 810-819.

Nykjaer A et al (1999): "An endocytic pathway essential for renal uptake and activation of the steroid 25-(OH) vitamin D3"; Cell, vol. 96, No. 4, pp. 507-515.

Ohlsson et al. 2003. "Increased circulating levels of proteinase 3 in patients with anti-neutrphilic cytoplasmic autoantibodies-associated systemic vasculitis in remission". Clin Exp Immunol, 131:528-535.

Parikh CR et al (2004): "Urinary interleukin-18 is a marker of human acute tubular necrosis"; Am J Kidney Dis; vol. 43, No. 3, pp. 405-414.

Parikh et al (2006): "Urine NGAL and IL-18 are predictive biomarkers for delayed graft function following kidney transplantation"; Am J Transplant, vol. 6, No. 7, pp. 1639-1645.

Parikh et al. 2005. "NGAL and IL-18: Novel early sequential predictive biomarkers of acute kidney injury after cardiac surgery". Abstract, contact view, American Society for Nephrology Renal Week, Abstract, contact view, American Society for Nephrology Renal Week, Abstract F-FC033.

Pawluczyk IZA & Harris (1999): "A Role for a novel 24p3-like protein in macrophage-mediated mesangial cell injury"; Abstract 59, Meeting of the Renal Association Apr. 22-23, 1999, Royal College of Physicians of Ireland, Dublin. Also published in Kidney International Meeting Abstracts, Blackwell Synergy D9 and D16.

Pawluczyk IZA et al (2003): "Macrophage-induced rat mesangial cell expression of the 24p3-like protein alpha-2-microglobulin-related protein"; Biochimica et Biophysica Acta, vol. 1645, pp. 218-227.

R414 Request for stay of proceedings to EPO, Mar. 5, 2009, from Opposition proceedings in EP 1 831 699 B1.

R414DK00 Decision from Legal Division; Aug. 12, 2009, from Opposition proceedings in EP 1 831 699 B1.

R414DK00 EPO resumes proceedings; Jul. 10, 2009, from Opposition proceedings in EP 1 831 699 B1.

R414DK00 Letter with withdrawal; Sep. 25, 2009, from Opposition proceedings in EP 1 831 699 B1.

R414DK00 Third party does not appeal; Sep. 28, 2009, from Opposition proceedings in EP 1 831 699 B1.

R414DK00 withdrawal DK; Sep. 23, 2009, from Opposition proceedings in EP 1 831 699 B1.

R414DK00 Withdrawal EN; Sep. 23, 2009, from Opposition proceedings in EP 1 831 699 B1.

Riordan et al. 2002. "Poisoning in children 4: Household products, plants, and mushrooms" Arch Dis Child 87: 403-406.

Roudkenar et al., Jan. 1, 2007, "Oxidative stress induced lipocalin 2 gene expression: Addressing its expression under the harmful conditions", Journal of Radiation Research, vol. 48, No. 1, pp. 39-44.

Rudd P.M. et al. (1999): "Glycosylation of natural human neutrophil gelatinase B. and neutrophil gelatinase B-associated lipocalin" Biochemistry 19991019 American Chemical Society US, vol. 38, No. 42, pp. 13937-13950.

Ryon et at (2002): "High expression in involuting reproductive tissues of uterocalin/24p3, a lipocalin and acute phase protein"; Biochemical Journal, vol. 367, pt. 1, pp. 271-277.

Scherberich JE, Wiemer J, Schoeppe W (1992): "Biochemical and immunological properties of urinary angiotensinase A and dipeptidylaminopeptidase IV. Their use as markers in patients with renal cell injury". Eur J Clin Chem Clin Biochem 30:663-668.

Solberg. 1994. Textbook of Clin Chem. Chapt 13 2nd ed, "Establishment and Use of Reference Values".

Sorof JM et al (1999): "Early initiation of peritoneal dialysis after surgical repair of congenital heart disease"; Pediatr Nephrol, vol. 13, No. 8, pp. 641-645.

Suzuki M et al (2008): "Neutrophil gelatinase-associated lipocalin as a biomarker of disease activity in pediatric lupus nephritis"; Pediatric Nephrology, vol. 23, No. 3, pp. 403-412.

Tang S, Leung JC, Abe K, Chan KW, Chan LY, Chan TM, Lai KN (2003): "Albumin stimulates interleukin-8 expression in proximal tubular epithelial cells in vitro and in vivo". J Clin Invest 111:515-527.

Thadhani et al. "Acute renal failure" NEJM, vol. 334, No. 22, pp. 1448-1460, 1996.

The defendant's amended version of EP 1831699; Jun. 18, 2008, Letter and amended claims, 3 pages.

The Merck Manual of patient symptoms—A concise practical guide to etiology, evaluation and treatment; Eds. Robert S Porter, Justin L. Kaplan, Barbara P. Homeier; Merck Research Laboratories, Whitehouse Station, NJ, USA, 2008; Online medical library: "Acute Renal Failure";(Longer list of causes of ARF), (8 pages).

The Merck Manual of patient symptoms—A concise practical guide to etiology, evaluation and treatment; Eds. Robert S Porter, Justin L. Kaplan, Barbara P. Homeier; Merck Research Laboratories, Whitehouse Station, NJ, USA, 2008; Online medical library: "Causes of acute interstitial nephritis";( List of causes of ATN), (one page).

The protocol on Jurisdiction and the recognition of Decisions in Respect of the Right to the Grant of a European Patent, Oct. 5, 1973.

Tuladhar et al. "Rapid Detection of Acute Kidney Injury by Plasma and Urinary Neutrophil gelatinase—associated Lipocalin After Cardiopulmonary Bypass" J Cardiovasc Pharmacol, vol. 53, No. 3, Mar. 2009, pp. 261-266.

Tuttle KR et al (2003): "Predictors of ARF after cardiac surgical procedures"; Am J Kidney Dis; vol. 41, No. 1, pp. 76-83.

Uttenthal. 2005. "NGAL: A marker molecule for the distressed kidney". CLI Nov, (two pages).

Uttenthal. 2007. "NGAL: how useful is the new marker of kidney damage". Clinical Laboratory International. (www.cli-online.com).

Vemula et al., Jun. 2004: "Expression profiling analysis of the metabolic and inflammatory changes following burn injury in rats", Physiol Genomics, vol. 18, No. 1, pp. 87-98.

Venge P et al (1994): "Soluble markers of allergic inflammation"; Allergy, vol. 49, No. 1, pp. 1-8.

Venge P, Carlson M, Fredens K, Garcia R (1990): "The 40 kD-protein. A new protein isolated from the secondary granules of human neutrophils". Joint International Conference on Leukocyte Biology, abstract. J Leukocyte Biol 1(suppl.):28.

Wagener G et al (2006): "Association between Increases in Urinary Neutrophil Gelatinase—associated Lipocalin and Acute Renal Dysfunction after Adult Cardiac Surgery"; Anesthesiology, vol. 105, pp. 485-491.

Wheeler D. et al. (2008): "Serum neutrophil gelatinase-associated lipocalin (NGAL) as a marker of acute kidney injury in critically ill children with septic shock". Crit care Med, vol. 36, No. 4, pp. 1297-1303.

Wu et al. 1998. "Analytical and clinical evaluation of new diagnostic tests for myocardial damage". Clinics Chimica Acta, 272, 11-21.

Xin C et al (2008): "Urine Neutrophil Gelatinase-Associated Lipocalin and Interleukin-18 Predict Acute Kidney Injury after Cardiac Surgery"; Renal Failure, vol. 30, pp. 904-913.

Xu and Venge. "Lipocalins as biochemical markers of disease" Biochim Biophys Acta vol. 1482, (2000); 298-307.

Xu SY, Carlson M, Engstrom A, Garcia R, Peterson CG, Venge P (1994): "Purification and characterization of a human neutrophil lipocalin (HNL) from the secondary granules of human neutrophils". Scand J Clin Lab Invest 54:365-376.

Yanagisawa et al., Nov. 2004, "Complementary DNA microarray analysis in acute lung injury included by lipopolysaccharide and diesel exhaust particles", Exp Biol Med, vol. 229, No. 10, pp. 1081-1087.

Yang CW et al (2001): "Pharmacological preconditioning with low-dose cyclosporine or FK506 reduces subsequent ischemia/reperfusion injury in rat kidney"; Transplantation, vol. 72, No. 11, pp. 1753-1759, (Abstract and list of references only).

Yilmaz et al. 2009: "Early prediction of urinary tract infection with urinary neutrophil gelatinase-associated lipocalin"; Pediatr Nephrol 24: 2387-2392.

Yndestad A et al (2009): "Increased systemic and myocardial expression of neutrophil gelatinase-associated lipocalin in clinical and experimental heart failure"; European Heart Journal, vol. 30, No. 10, pp. 1229-1236.

Zanardo G et al (1994): "Acute renal failure in the patient undergoing cardiac operation. Prevalence, mortality rate, and main risk factors"; Journal of thoracic and cardiovascular surgery; vol. 107, No. 6, pp. 1489-1495.

Zappitelli et al. 2007. "Urine neutrophil gelatinase-associated lipocalin in an early marker of acute kidney injury in critically ill children: a prospective cohort study"; Crit Care, vol. 11, pp. R84.

Zerega B et al (2000): "Expression of NRL/NGAL (neu-related lipocalin/neutrophil gelatinase-associated lipocalin) during mammalian embryonic development and in inflammation"; Eur J Cell Biol.; vol. 79, No. 3, pp. 165-172.

Zhao H, Ito A, Sakai N, Matsuzawa Y, Yamashita S, Nojima H (2006): "RECS1 is a negative regulator of matrix metalloproteinase-9 production and aged RECS1 knockout mice are prone to aortic dilation". Circ J 70:615-624.

Zhu T et al (2002): "Cyclosporine A protects against apoptosis in ischaemic/reperfused rat kidneys"; Clin exp pharmacol physiol; vol. 29, No. 9, pp. 852-854.

Zweig & Campbell. (1993): "Receiver-Operating Characteristic (ROC) Plots: A Fundemental Evaluation Tool in Clinical Medicine". Clin Chem 39/4, 561-577.

Eriksen BO et al (2003): "Prediction of acute renal failure after cardiac surgery: retrospective cross-validation of a clinical algorithm"; Nephrol Dial Transplant, vol. 18, No. 1, pp. 77-81.

Elneihoum et al., "Leukocyte Activation in Atherosclerosis: Correlation with Risk Factors," Atherosclerosis 131:79-84, 1997.

BioPorto Diagnostics A/S Press Release, "A/S to Launch Analysis for Novel Marker of Acute Kidney Injury," Sep. 22, 2005. (English Translation), one page.

Moore RE, "A Historical Perspective on the Clinical Diagnostic Laboratory," *Molecular Diagnostics for the Clinical Laboratorian 2nd Ed*. Humana Press, p. 4-5, 2005.

Product Insert for NGAL Elisa Kit #036, BioPorto Diagnostics A/S, p. 1-12, May 2010.

Product Insert for NGAL Rapid ELISA Kit #037, BioPorto Diagnostics A/S, p. 1-10, Revision NR2007-12-EN, Dec. 2007.

Product Insert for NGAL Rapid ELISA Kit #037, BioPorto Diagnostics A/S, p. 1-84, May 2010.

* cited by examiner

DIAGNOSTIC TEST FOR RENAL INJURY

This patent application is the National Stage of International Application No. PCT/DK2008/050069, filed Mar. 18, 2008, which claims the benefit of priority from U.S. Provisional Patent Application Ser. No. 60/919,277, filed Mar. 21, 2007, teachings of each of which are herein incorporated by reference in their entirety.

FIELD OF THE INVENTION

The present invention relates to the diagnosis and monitoring of a recently occurred or ongoing injurious process in a mammal that is affecting the kidneys and may lead to acute renal failure (ARF), hereinafter also synonymously referred to as acute renal dysfunction (ARD). As such it is relevant to internal medicine and in particular to critical or intensive care medicine, but also to surgery, oncology and diagnostic imaging, where procedures that may injure the kidneys are carried out. It is also relevant to veterinary medicine and surgery and to the study of renal pathophysiology and noxious influences on the kidney in laboratory animals.

BACKGROUND OF THE INVENTION

The present invention relates to the diagnostic use of a new marker molecule for renal pathology that appears in both blood and urine, to detect the presence of significant renal injury, hereinafter used in the sense of injury to constituent cells of the kidney, including but not limited to renal tubular cell injury, in a human being or mammal. The marker molecule is neutrophil gelatinase-associated lipocalin (NGAL), also known as neutrophil lipocalin (NL; HNL in the case of human neutrophil lipocalin), lipocalin 2 (LCN2), 25-kDa alpha2-microglobulin-related protein (in the rat) or 24P3 (in the mouse). In the rat, it has also been referred to as neu-related lipocalin (NRL), as its gene is overexpressed in mammary tumors initiated by the neu (HER2/c-erbB-2) oncogene (Stoesz and Gould, 1995). NGAL is a 25-kDa glycoprotein first isolated from the granules of neutrophil polymorphonuclear leukocytes (Triebel et al., 1992; Kjeldsen et al., 1993). It contains a disulfide bridge and forms a proportion of dimers and a smaller proportion of trimers. Part of the total secreted NGAL is associated with 92-kDa human neutrophil type IV collagenase, also called matrix metalloproteinase 9 (MMP-9) or gelatinase B, either as an NGAL monomer forming a complex of apparent kDa 115, (Monier et al., 2000; Yan et al., 2001) or as an NGAL dimer, forming a complex of apparent kDa 125 (Yan et al., 2001). These complexes have been identified in the urine of patients with a variety of cancers, including cancers of the prostate, bladder, kidney and breast.

NGAL was initially disclosed as a marker of neutrophil activation, being released into the blood when invading microorganisms, in particular pyogenic bacteria, cause degranulation of the neutrophils and exocytosis of the granule proteins. As such, the measurement of elevated levels of NGAL in a serum sample from a human is believed to indicate that the individual is suffering from an inflammatory process, especially one caused by a bacterial infection (U.S. Pat. No. 6,136,526; PCT application WO95/29404). In this respect, but in contradiction to its claimed specific derivation from neutrophils, NGAL (24P3) was identified as an acute phase protein of type 1 in the mouse, where expression was mainly located in the liver during the acute phase response (Liu and Nilsen-Hamilton, 1995).

U.S. Patent Application 2004/0219603 discloses the use of NGAL as a urinary biomarker for detecting the early onset of renal tubular cell injury. U.S. Patent Application 2005/0272101 discloses the use of NGAL in blood serum for the same purpose. However, neither disclosure describes how renal tubular cell injury can be discriminated from systemic inflammation, or bacterial infection, or cancers as the cause of the elevated NGAL level. The present inventors have previously filed a PCT application WO2006/066587 which discloses how NGAL levels in urine or blood plasma or serum can be separated into lower elevations that are not diagnostic of renal injury and higher elevations that are, by defining cutoff levels of NGAL in these fluids that must be exceeded in order for the NGAL measurement to be diagnostic of renal injury leading to ARF or ARD. WO2006/066587, which is hereby incorporated into the present application by reference in its entirety, takes into account the fact that NGAL levels in bodily fluids may also be elevated in inflammations, infections and certain cancers, but usually to lower values than those associated with renal injury leading to ARF or ARD. However, a small number of patients with severe infection and/or cancers may show NGAL levels that are above the cutoff level used to diagnose renal injury, even though they do not develop renal injury during their hospitalization, while a few patients develop a minor degree of ARD even though their NGAL levels did not exceed the cutoff. When a cutoff level is used, these two types of borderline cases may give rise to false positive diagnoses of renal injury or false negative diagnoses of absence of renal injury, respectively.

It is the purpose of the present invention to provide a reliable means of distinguishing between rises of NGAL in bodily fluids that are due to renal injury and those that are due to non-renal causes, without resorting to the use of a cutoff value for the concentration of NGAL in a given bodily fluid.

SUMMARY OF THE INVENTION

The invention depends on our observation that NGAL originating from renal injury is secreted into the urine to achieve a higher concentration in the urine than that achieved in the blood plasma. Conversely, NGAL secreted into the blood from the extra-renal sources such as neutrophil polymorphonuclear leukocytes in infection, or from certain adenocarcinomas, typically gives rise to a higher concentration in the blood plasma than in the urine.

Because the expression and secretion of NGAL by the kidney is low in the basal state, the median basal concentration of NGAL in the urine of healthy human subjects is about 5 ng/mL. NGAL is also released into the blood by neutrophils and possibly by other tissues, to give a median basal concentration in the plasma of about 60 ng/mL. This means that the median ratio of the NGAL concentration in the urine to that in the plasma is about 0.08. No healthy human subject has been observed by us to have urine:plasma ratio of NGAL concentrations greater than 0.3.

In renal injury, NGAL is secreted into the urine to a greater extent than into the blood. This will increase the urine:plasma NGAL concentration ratio above the ratios seen in healthy subjects. Accordingly, the present invention comprises diagnosing renal injury by:

i) determining the concentration of NGAL in a sample of urine taken from a mammal;

ii) determining the concentration of NGAL in plasma or serum from a sample of blood taken from the same mammal immediately before, during or immediately after the period of time over which the urine sample was collected;

iii) Calculating the ratio of the NGAL concentration in the urine to that in the plasma or serum and comparing the value of the ratio obtained with a cutoff value determined from the range of ratios observed in mammals of the same species with and without evidence of renal injury, so that a value greater than the cutoff value indicates that renal injury has occurred.

The inverse ratio, that is, the NGAL concentration in plasma or serum divided by that in urine, can also be calculated and compared with a similarly determined cutoff value for such an inverse ratio. In that case, all the ratios used will be the reciprocals of those mentioned in iii) above, and this makes no difference to the practice of the invention, except that a value of the inverse ratio that is lower than the "inverse" cutoff value will indicate that renal injury has occurred.

The method described has the advantage of being independent of the absolute concentrations of NGAL in urine and plasma or serum, so that these do not have to exceed a certain cutoff value of the absolute concentration in order for the ratio between them to be diagnostic of renal injury. This makes it possible to diagnose renal injury before this has progressed to an extent that gives rise to levels of NGAL in urine and plasma or serum above cutoff values determined for the absolute concentrations in these bodily fluids, which have been set high in order to exclude the majority of the raised levels of NGAL that can be observed in the non-renal disorders mentioned.

The method of the present invention is particularly useful in patients admitted to intensive or critical care departments and will also be useful in patients who, while not being critically ill, have suffered a well-defined insult such as a surgical operation that may lead to ischemic injury of the kidney or have been exposed to a nephrotoxic agent, such as a chemotherapeutic or antimicrobial agent or intravenously administered contrast medium for diagnostic imaging. In these cases the early identification of patients whose kidneys have been affected by the procedure and who are therefore at risk of ARF may allow for an earlier and more intensive intervention to prevent the development of ARF. The method will also be useful in veterinary medicine, the investigation of renal pathophysiology in experimental animals, and the testing of candidate therapeutic or diagnostic agents for nephrotoxicity in laboratory animals.

Levels of NGAL in bodily fluids are preferably determined by means of one or more molecules that bind specifically to the NGAL of the species in question, including immunochemical methods that use one or more polyclonal or monoclonal antibodies against NGAL. Examples of such methods include, but are in no way limited to, a sandwich ELISA (enzyme-linked immunosorbent assay), a lateral flow immunochromatographic method, an antibody-coated dipstick, or an automated immunochemical method based on antibody-coated microparticles.

Receiver operating characteristics (ROC) curve for the urine:plasma NGAL concentration ratio with respect to the diagnosis of renal injury leading to acute renal failure in 458 paired samples of urine and plasma from 90 adult patients admitted to a hospital intensive care unit.

Figure 2A:
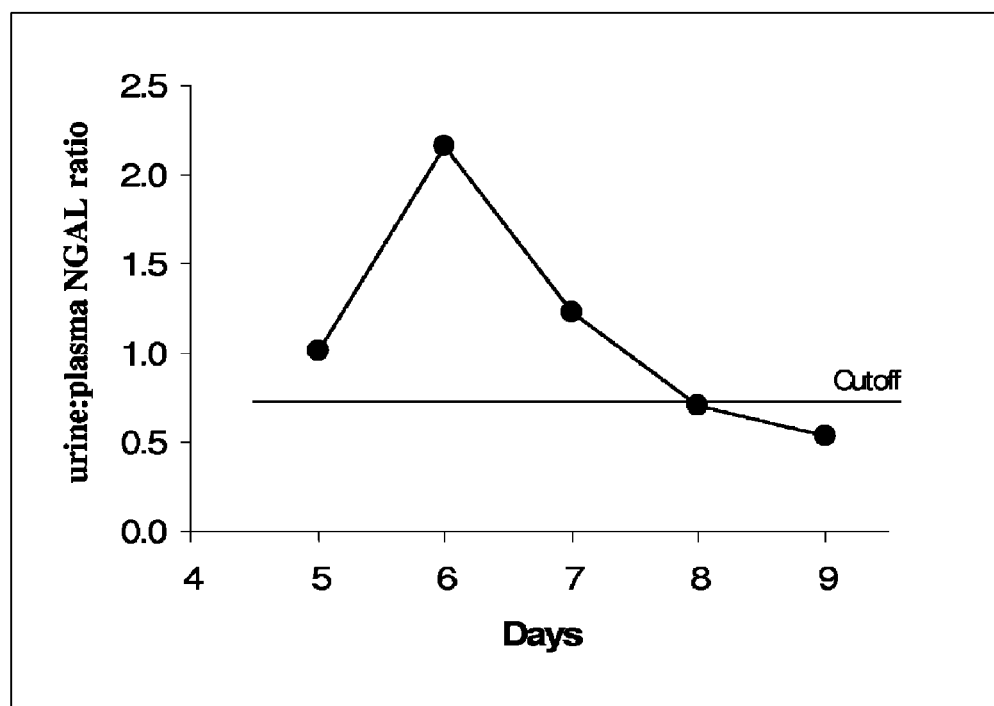
Figure 2B:
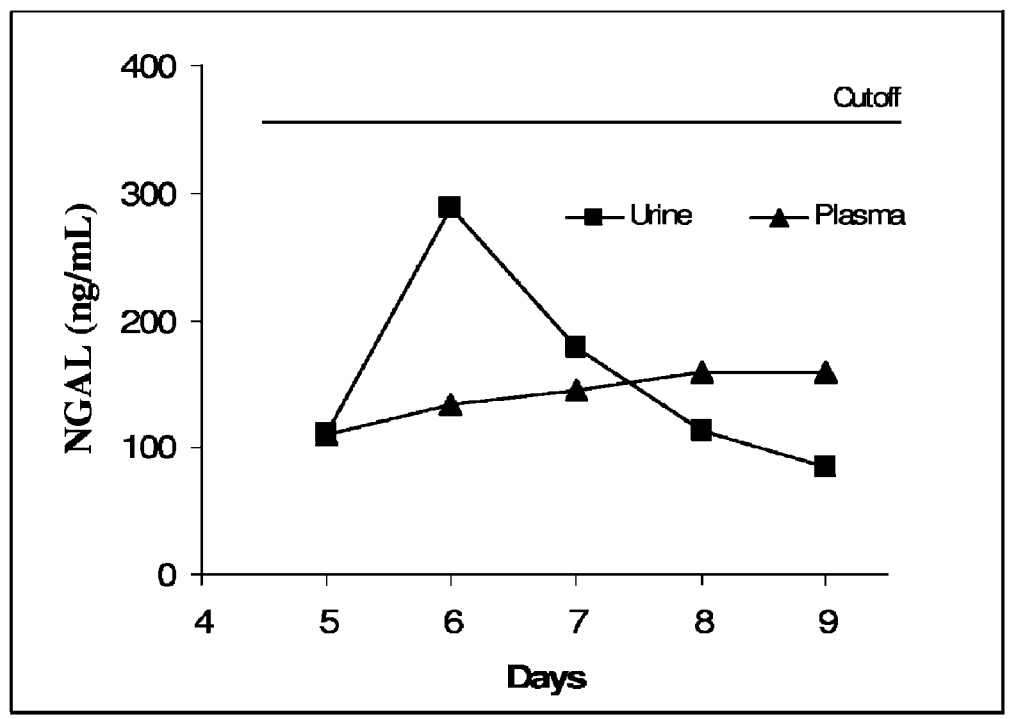

FIGS. 2a and 2b

Time course of the urine:plasma NGAL concentration ratio (FIG. 2a) and urine and plasma NGAL concentrations (FIG. 2b) in a patient with a minor episode of renal injury. On day 5, the urine:plasma NGAL concentration was approximately 1, but rose to over 2 on the following day. The cutoff value of 0.73 for the ratio (FIG. 2a) is shown. The absolute concentrations of NGAL in the urine and plasma did not rise above the cutoff value of 355 ng/mL determined for the patient group studied (FIG. 2b), which would be indicative of ARF for the NGAL concentration in either of these bodily fluids. The plasma creatinine (not shown) rose from the upper limit of normal on days 5 and 6 to peak on day 8, 48 hours after the peak of urine:plasma NGAL concentration ratio.

Figure 3A:
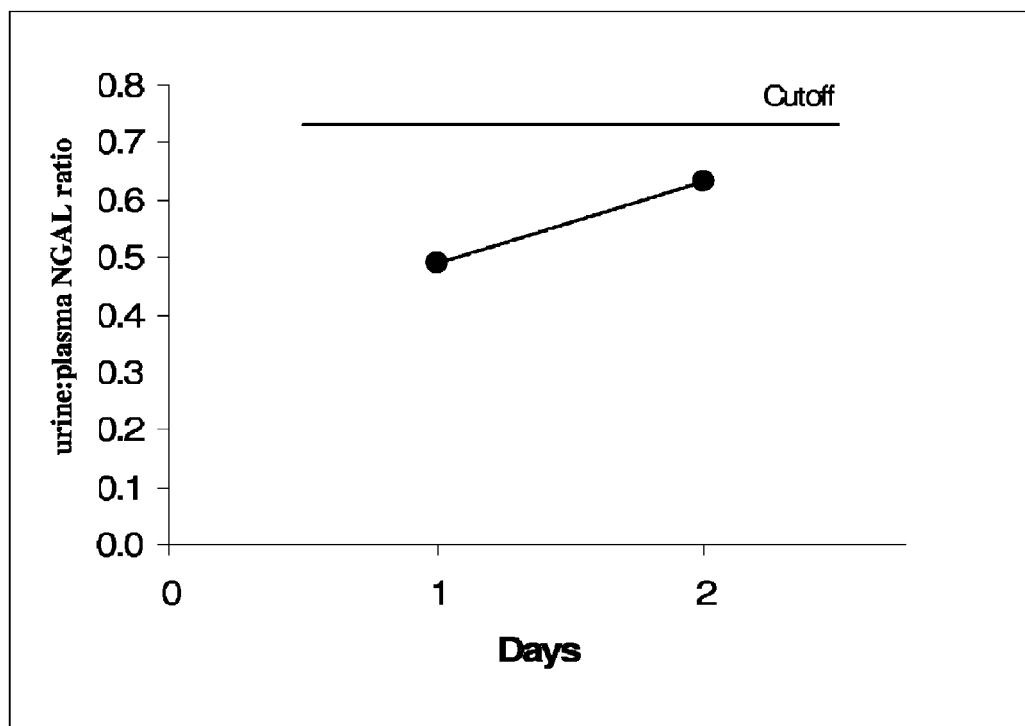
Figure 3B:
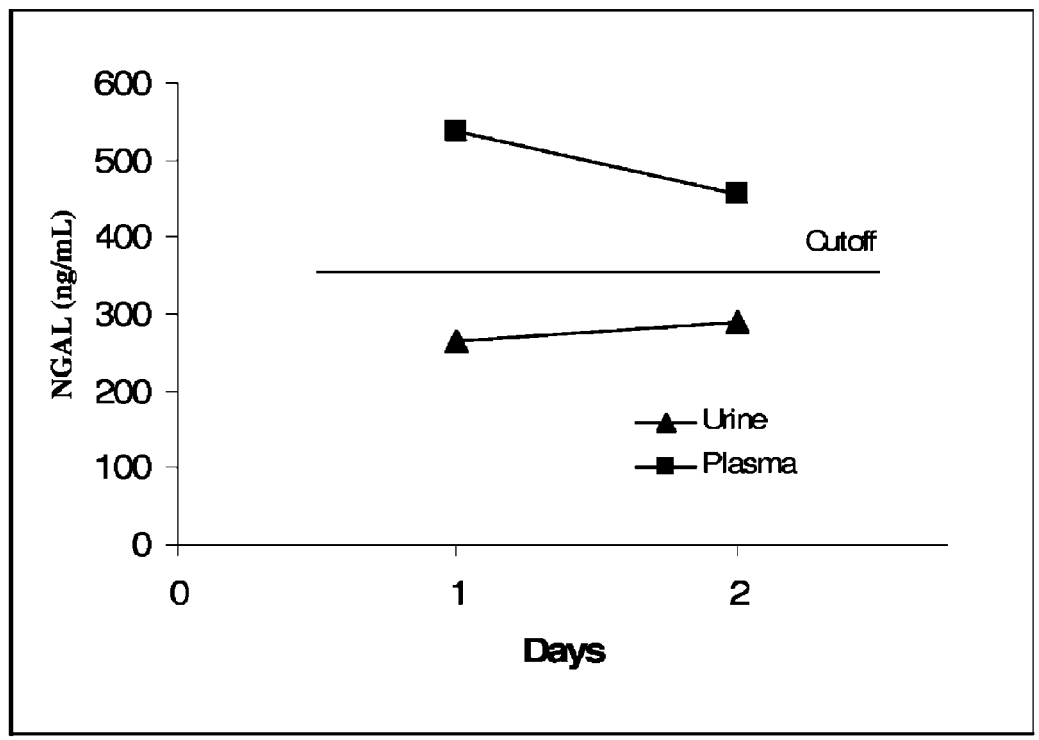

FIGS. 3a and 3b

The urine:plasma NGAL concentration ratio (FIG. 3a) and urine and plasma NGAL concentrations (FIG. 3b) in a patient who did not develop ARF. Concurrent conditions (intestinal perforation and peritonitis) led to a plasma NGAL concentration that was well above the cutoff value of 355 ng/mL (FIG. 3b) that would make it independently diagnostic of ARF in this patient group, but the fact that the urine:plasma NGAL concentration ratio remained below the cutoff value of 0.73 for the ratio (FIG. 3a) demonstrated that the NGAL was not of renal origin. The plasma creatinine (not shown) remained low in the normal range.

Figure 4A:
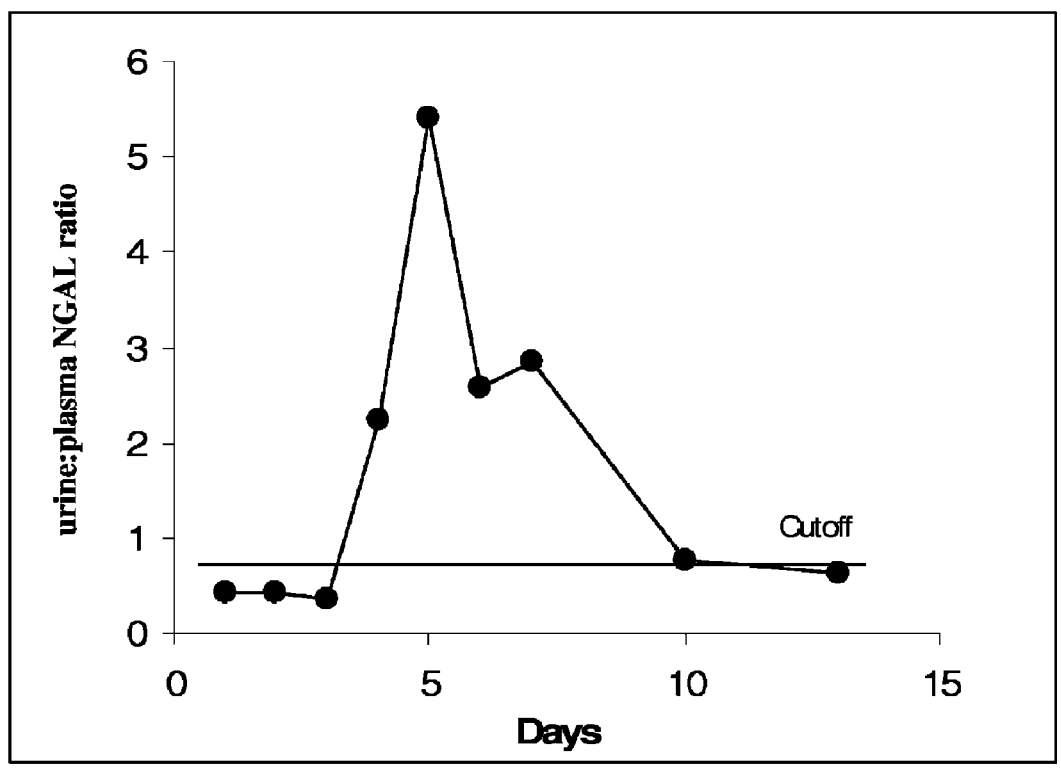
Figure 4B:
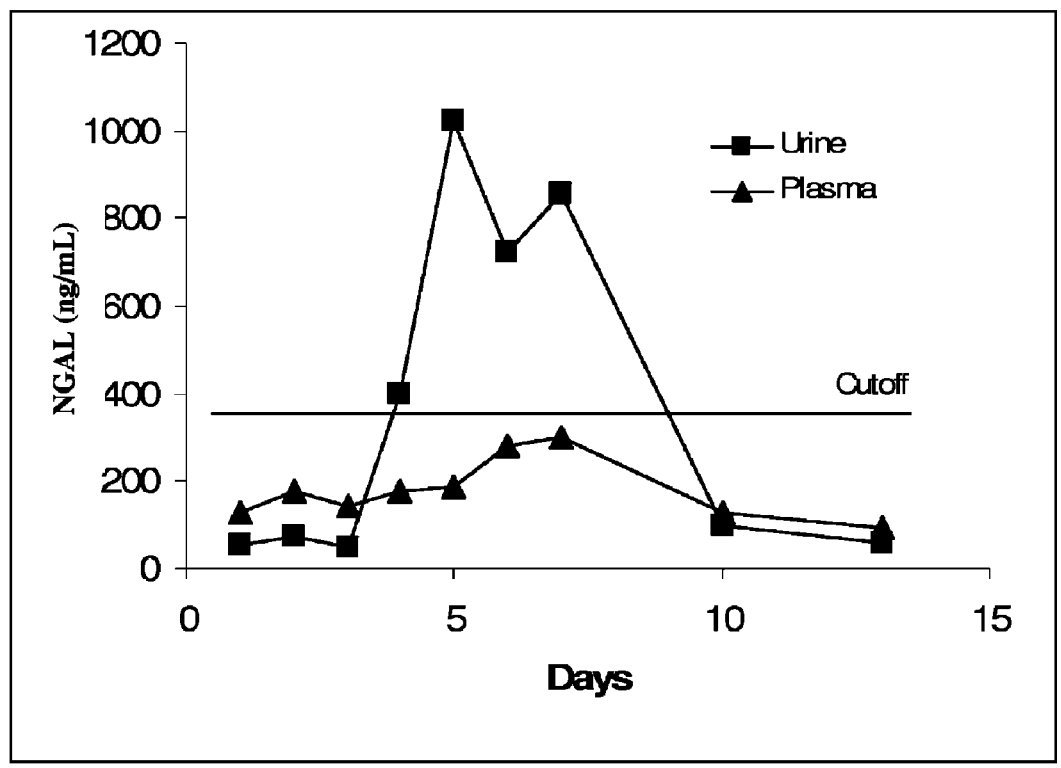

FIGS. 4a and 4b

Time course of the urine:plasma NGAL concentration ratio (FIG. 4a) and urine and plasma NGAL concentrations (FIG. 4b) in a patient with a typical episode of renal injury due to sepsis. The urine:plasma NGAL concentration ratio rose from normal values on days 1 to 3 to exceed the cutoff of 0.73 (FIG. 4a) on day 4 and peaking on day 5, while the plasma creatinine (not shown) peaked on day 6. Whereas the urinary NGAL concentrations reached would have been independently diagnostic of ARF, the plasma NGAL concentrations never rose above the cutoff of 355 ng/mL (FIG. 4b) determined for the patient group studied and would not have been independently diagnostic of ARF.

FIG. 5a+5b

Figure 5A:
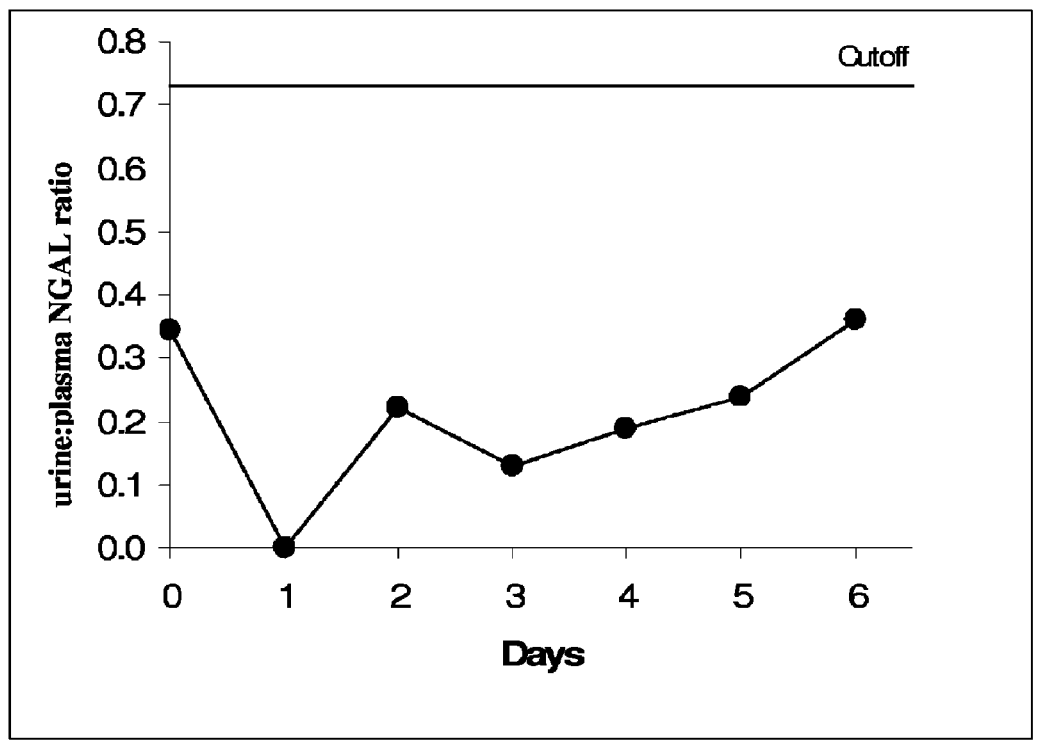
Figure 5B:
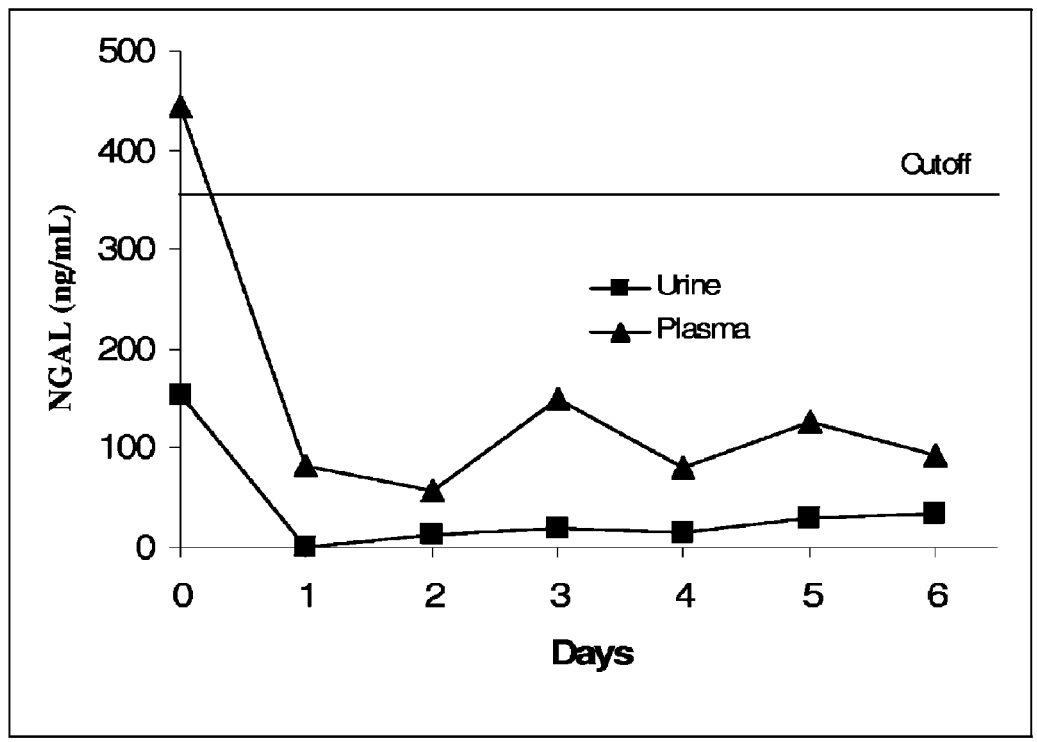

Time course of the urine:plasma NGAL concentration ratio (FIG. 5a) and the urine and plasma NGAL concentrations (FIG. 5b) in a patient who did not develop ARF. The patient was admitted with pneumonia and dehydration, resulting in a plasma NGAL concentration on day 0 that was higher than the previously determined cutoff value of 355 ng/mL, which would have been independently diagnostic of actual or impending ARF in this patient group. However, this was contradicted by the urine:plasma NGAL concentration ratio, which remained well below the cutoff value of 0.73 (FIG. 5a). The plasma creatinine (not shown) fell from just below the upper limit of normal on day 0 to low basal values on the following days.

DETAILED DESCRIPTION OF THE INVENTION

In a series of critically ill patients admitted to intensive care, we have observed that NGAL originating from renal injury is secreted into the urine to achieve a higher concentration in the urine than that achieved in the blood plasma or serum. Conversely, NGAL secreted into the blood from the extra-renal sources such as neutrophil polymorphonuclear leukocytes in infection, or from certain adenocarcinomas, typically gives rise to a higher concentration in the blood plasma or serum than in the urine.

Free NGAL in the blood is filtered by the renal glomeruli and partially reabsorbed from the glomerular filtrate by the distal convoluted tubules. Thus, an increase in the NGAL concentration in the blood will be reflected, but relatively weakly, by a smaller increase in the NGAL concentration in the urine. If NGAL is released directly into the glomerular filtrate by injured proximal tubule or other cells, this will appear in the urine at a higher concentration than in the blood, some NGAL entering the blood by reabsorption in the distal convoluted tubules and/or by diffusion to the blood from the injured cells. Injury to the renal tubules is associated with a reduced reabsorption of NGAL and a number of other small protein molecules, this providing a further reason why the rise of NGAL concentration in urine in renal injury is greater than that in plasma or serum.

Because the expression and secretion of NGAL by the kidney is low in the basal state, the median basal concentration of NGAL in the urine of healthy human subjects is about 5 ng/mL. A high proportion of the free NGAL in the blood that is filtered by the glomeruli is reabsorbed by the renal tubules, thus maintaining the low basal urinary concentration of NGAL. NGAL is normally present in the blood plasma or serum at higher levels, corresponding to a median basal concentration of about 60 ng/mL. This is attributed to the release of NGAL into the blood by neutrophils and possibly to a slight extent by other tissues. The median ratio of the NGAL concentration in the urine to that in the plasma is therefore about 0.08. No healthy human subject has been observed by us to have a urine:plasma ratio of NGAL concentrations greater than 0.3. Thus in an embodiment of the present invention the cutoff value of the ratio of the urinary concentration of NGAL to the plasma concentration of NGAL is preferably a value of 0.30 or higher, such as 0.33, or a higher value such as any value from 0.33 to 0.73 inclusive, or a higher value such as any value from 0.73 to 1.14 inclusive, or a higher value such as any value above 1.14.

In renal injury as herein defined, NGAL is secreted into the urine to a greater extent than into the blood. At the same time, renal tubular reabsorption of NGAL is impaired. Both phenomena contribute to an increase in the urine:(plasma or serum) NGAL concentration ratio above the ratios seen in healthy subjects and patients without renal injury.

It is evident that increase in the urine:(plasma or serum) NGAL concentration ratio consequent on renal injury will apply not only to human subjects but also to any mammal with renal structure and function similar to that of human beings. Accordingly, the present invention comprises diagnosing renal injury by:

i) determining the concentration of NGAL in a sample of urine taken from the mammal;

ii) determining the concentration of NGAL in plasma or serum from a sample of blood taken from the same mammal immediately before, during or immediately after the period of time over which the urine sample was collected;

iii) Calculating the ratio of the NGAL concentration in the urine to that in the plasma or serum and comparing the value of the ratio obtained with a cutoff value determined from the range of such ratios observed in mammals of the same species with and without evidence of renal injury, so that a value greater than the cutoff value indicates that renal injury has occurred.

The inverse ratio, that is, the NGAL concentration in plasma or serum divided by that in urine, can also be calculated and compared with a similarly determined cutoff value for such an inverse ratio. In that case, all the ratios used will be the reciprocals of those mentioned in iii) above, and this makes no difference to the practice of the invention, except that a value of the inverse ratio that is lower than the "inverse" cutoff value will indicate that renal injury has occurred. Thus in an embodiment of the present invention the cutoff value of the ratio of the plasma or serum concentration of NGAL to the urinary concentration of NGAL is preferably a value of 3.33 or lower, such as 3.0, or a lower value such as any value from 1.37 to 3.0 inclusive, or a lower value such as any value from 0.88 to 1.37 inclusive, or a lower value such as any value from 0.88 to zero, these values being the approximate reciprocals of the corresponding cutoff values described above.

The method described has the advantage of being independent of the absolute concentrations of NGAL in urine and plasma or serum, so that these do not have to exceed a certain cutoff value of the absolute concentration in order for the ratio between them to be diagnostic of renal injury. This makes it possible to diagnose renal injury before this has progressed to an extent that gives rise to absolute levels of NGAL in urine and plasma or serum above cutoff values for these bodily fluids, which have been set high in order to exclude the majority of the raised levels of NGAL observed in non-renal disorders.

Although step ii) of the invention can be performed by measuring NGAL in either blood plasma or blood serum, in the preferred embodiment of the invention NGAL is measured in plasma from anticoagulated whole blood rather than in serum from coagulated blood. The concentration of NGAL is measured either in plasma separated from the blood sample prior to analysis, or in plasma separated from the blood as an integral part of an automated or semi-automated analytical procedure in which the sample material applied is anticoagulated whole blood. Measurement of NGAL in plasma rather than serum has the advantage of permitting the analysis to be performed immediately after collecting the blood sample, without any lapse of time to allow the blood to clot and serum to be formed. It has the additional advantage of avoiding any risk of NGAL being released into the serum from neutrophils in the blood sample during the clotting process, which may occur during some procedures for the preparation of serum.

In a study of unselected adult patients admitted to intensive care, we have found that the ratio of the NGAL concentration in a sample of urine to that in a sample of plasma collected at the same time provides a very good indication of whether or not the patient has suffered a renal injury that has led to ARF or ARD or will lead to ARF or ARD during the following day or days. This indication is independent of the absolute values of the NGAL concentrations in urine or plasma. Notwithstanding, a raised urine:plasma NGAL concentration ratio will almost certainly imply that the urinary NGAL concentration is above the normal range for healthy individuals, as a fall in the plasma NGAL concentration to below the normal range is a very rarely observed. The urine:plasma NGAL concentration ratio is markedly elevated in patients with ARF or destined to develop ARF within the next 24 hours, while this ratio rarely exceeds the normal range in patients who do not develop ARD during their admission, even though the absolute values of NGAL concentrations may be elevated above normal in both urine and plasma.

Because of i) the variability of patients and the many different diseases and conditions that occasion their admission to intensive care, ii) occasional logistic difficulties with the timing of sample collection under the circumstances of intensive care, and iii) the imprecision in the clinical diagnosis of ARF and ARD and the biochemical diagnosis of ARD from serum creatinine values, the interpretation of the urine: plasma NGAL concentration ratio still requires comparison of the ratio with an empirically determined cutoff value to achieve the best distinction between those higher ratios that indicate renal injury leading to ARF or ARD and those lower ratios that do not.

Data from the clinical study are given in Example 1 below. 458 paired, simultaneous samples of urine and plasma were obtained from 90 patients who could be classified from other data as either being affected or not being affected by an episode of ARF or ARD at the time of sampling or during the following 24 hours. Receiver operating characteristics (ROC)

analysis of the data for these samples showed that using a cutoff value for the urine:plasma NGAL concentration ratio of 0.73 gave the best overall discrimination between ARF/ARD and non-ARF/ARD for a single paired test. Ratios above 0.73 were predictive of actual or impending ARF/ARD with a positive predictive value of 96.3%. Ratios below 0.73 were predictive of absence of actual or impending ARF/ARD with a negative predictive value of 97.4%. The diagnostic sensitivity and specificity were 96.3% and 97.4%, respectively. The cutoff value of 0.73 was also close to the maximum of the median values of all the ratios observed in each individual patient without ARF/ARD (0.74).

The range of cutoff values that might be obtained in similar studies on other patient populations was estimated from the minimum value of the ratios observed in individual patients with ARF or ARD (0.33) and the maximal value of the ratios observed in patients without ARF or ARD (1.14). With the present results, a cutoff of 0.33 gives a positive predictive value of 75.9%, a negative predictive value of 100%, a diagnostic sensitivity of 100% and a diagnostic specificity of 77.1%. A cutoff of 1.14 would give a positive predictive value of 100%, a negative predictive value of 92.7%, a diagnostic sensitivity of 89.1% and a diagnostic specificity of 100%.

Accordingly, the cutoff level above which the urine:plasma NGAL concentration ratio is predictive of ARF or ARD is preferably a value of 0.30 or higher, such as 0.33, or any value from 0.33 to 0.73 inclusive, at which latter value the diagnostic sensitivity, specificity and positive and negative predictive values are all above 95%, or any value from 0.73 to 1.14 inclusive, at which latter value the positive predictive value is 100%, or any value greater than 1.14, at all of which the positive predictive value remains 100%.

A further aspect of the present invention is that the method can be used to monitor patients throughout the course of an illness or at various times after a diagnostic or therapeutic intervention that carries a risk of provoking ARF. Comparison of the measured urine:plasma NGAL concentration ratios with the cutoff value will determine when the patient has suffered renal injury and is at risk of developing ARF. The intervals at which samples of bodily fluids are taken for monitoring can be short, thus providing the earliest possible indication of renal injury and permitting the early institution of preventive or therapeutic measures. Monitoring of the urine:plasma NGAL concentration ratio for this purpose is preferably carried out at intervals not longer than 24 hours, and more preferably at shorter intervals down to a suggested period of not longer than 3 h, or even shorter, such as 30 minutes or 1 hour, for instance if a potential renal insult is known to have occurred, e.g. during a surgical or medical procedure.

An additional advantage of the present invention is that a cutoff value for the urine:plasma NGAL concentration ratios determined by one analytical technique can be applied to results obtained by a different analytical technique. This is because the concentration ratios obtained, unlike absolute concentration values, will be independent of the analytical techniques used and possible differences in their calibration, always provided that the analytical method shows a satisfactory linearity and is not influenced by differences in the composition of urine, plasma or serum that are not differences in the NGAL concentration.

The method of the present invention is particularly useful in patients admitted to intensive or critical care departments, or in any patient who is affected by a serious inflammatory, infective or neoplastic disease or disorder, which in itself or through its complications carries a high risk of causing renal injury leading to ARF or ARD. In this situation, the inflammatory, infective or neoplastic disorder may itself give rise to an elevated NGAL concentration before any renal injury has occurred. This elevation will usually be more marked in plasma than in urine, and the plasma level may in certain circumstances exceed the cutoff level above which the NGAL concentration in plasma is normally regarded as diagnostic of renal injury leading to ARD. The method of the present invention will not diagnose such a patient as having a renal injury leading to ARD until such time as the urinary concentration of NGAL rises to give a urine:plasma NGAL concentration ratio above the diagnostic cutoff value determined for this ratio, thus providing, in these patients, greater diagnostic specificity for renal injury leading to ARD than plasma or urinary levels of NGAL can separately provide.

The method of the present invention will also be useful in patients who, while not being critically ill, have suffered a well-defined insult such as a surgical operation that may lead to ischemic injury of the kidney or have been exposed to a nephrotoxic agent, such as a chemotherapeutic or antimicrobial agent or intravenously administered contrast medium for diagnostic imaging. In these cases the early identification of patients whose kidneys have been affected by the procedure and who are therefore at risk of ARF may allow for an earlier and more intensive intervention to prevent the development of ARF.

The method of the present invention will also be useful in veterinary medicine, the investigation of renal pathophysiology in experimental animals, and the testing of candidate therapeutic or diagnostic agents for nephrotoxicity in laboratory animals.

Measurement of NGAL in a sample of bodily fluid, such as a sample of urine, plasma or serum, can be performed by any method that provides satisfactory analytical specificity, sensitivity and precision. Preferred methods are binding assays using one or more binding molecules specific to NGAL and capable of binding to NGAL from the mammalian species from which the samples are obtained. Such binding molecules include, but are not limited to, polyclonal or monoclonal antibodies against NGAL or specific NGAL binding molecules generated by other means.

In a preferred method, monoclonal antibodies raised against recombinant NGAL from the mammalian species to be analyzed are used. One antibody is linked to a solid support to capture NGAL from a sample, such as a urine sample, a blood plasma or serum sample, while the other is labeled with at least one of a variety marker substances or chemical moieties, including but not limited to a chromophore, dye complex, fluorophore, electrochemical or chemoluminescence marker, or biotin or enzyme, that can be detected by any of many methods known to those skilled in the art. The solid support may e.g. be a polystyrene or polyvinyl chloride surface for enzyme-linked immunosorbent assay (ELISA), or latex (polystyrene) particles, or a filter frit composed of compressed polyethylene particles, or a porous nitrocellulose matrix, or indeed any suitable support used in immunochemical analyses. Particles coated with molecules that bind specifically to NGAL can also be used to determine NGAL concentrations in a sample by particle-enhanced turbidimetric or nephelometric methods, whether performed manually or by automated methods.

A preferred means for measuring NGAL in accordance with the present invention in a sample of urine or blood includes a dipstick, lateral flow (immunochromatographic) or minicolumn test, or a rapid time-resolved immunofluorometric assay, or a two-photon excitation microparticle-based immunoassay, all of which methods allow for the rapid, near-subject analysis of a sample. As will be understood by those of skill in the art upon reading this disclosure, however, other means of measuring NGAL can be used, including automated methods in central laboratories in which the apparatus permits the random access of samples for urgent analysis.

In a preferred embodiment, the method of the invention does not comprise a surgical, therapeutic or diagnostic step practiced on the human body.

The following non-limiting examples are provided to further illustrate the present invention.

EXAMPLES

Example 1

Diagnostic Power with Respect to ARF or ARD of the Urine:Plasma NGAL Concentration Ratio in 458 Paired Urine and Plasma Samples from 90 Adult Patients Admitted to Intensive Care NGAL was determined (by means of an NGAL ELISA kit providing the sandwich ELISA described in Example 5) in 458 paired samples of urine and plasma collected each morning from a total of 90 patients admitted to a hospital intensive care unit. On the basis of discharge summaries and the results of routine blood tests, the patients were classified (blindly with respect to NGAL data) into those with one or more episodes of ARF or ARD during their admission (37 patients, giving 192 paired samples associated with episodes of ARF or ARD at the time of sampling or 24 hours later) and those without episodes of ARF or ARD (53 patients, 266 paired samples). The median urine:plasma NGAL concentration ratio in the sample pairs associated with an episode of ARF or ARD was 3.18 (range 0.33 to 40.02), while that in sample pairs not associated with ARF or ARD was 0.20 (range 0.01 to 1.14).

The median, maximum and minimum ratios were recorded for each individual patient, and the median and ranges for these values determined for all the patients with and without ARF or ARD. For the patients with ARF or ARD, the median of median ratios was 3.17 (range 1.53 to 5.73), the median of minimum ratios was 1.18 (range 0.33 to 1.72) and the median of maximum ratios was 16.45 (range 16.45 to 40.02). For the patients without ARF or ARD, the median of median ratios was 0.19 (range 0.10 to 0.34), the median of minimum ratios was 0.05 (range 0.01 to 0.07) and the median of maximum ratios was 0.74 (range 0.60 to 1.14).

Figure 1:
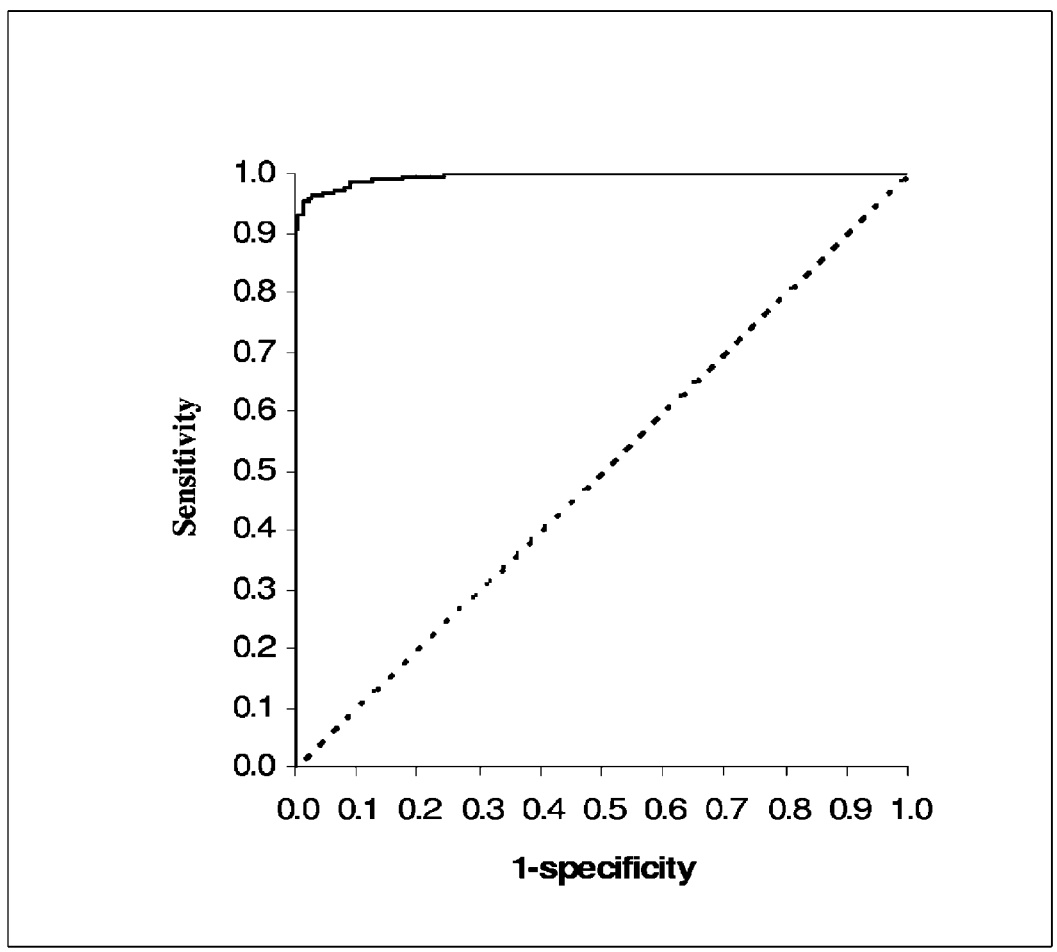
FIG. 1

The diagnostic power with respect to ARF and ARD of urine:plasma NGAL concentration ratio was determined by plotting the ROC curve shown in FIG. 1. The area under the curve was 0.991 and the cutoff value, above which the urine:plasma NGAL concentration ratio was diagnostic of actual or impending ARF or ARD with the best overall diagnostic performance characteristics, was determined to be 0.73. With this cutoff, the diagnostic sensitivity was 96.3%, the diagnostic specificity was 97.4%, the positive predictive value was 96.3% and the negative predictive value was 97.4%. However, other cutoffs could be chosen in order to improve certain diagnostic performance characteristics at the expense of the others. For example, a cutoff of 0.33, the minimum ratio observed in patients with ARF or ARD, would give a diagnostic sensitivity and a negative predictive value of 100%, while the diagnostic specificity would fall to 77.1% and the positive predictive value to 75.9%. A cutoff of 1.14, the maximum ratio observed in patients without ARF or ARD, would give a positive predictive value and a diagnostic specificity of 100%, while the negative predictive value would be 92.7% and the diagnostic sensitivity 89.1%.

Example 2

NGAL Dipstick Test

The analytical area of a dipstick comprised of a polystyrene surface is coated with a capture antibody against human NGAL. An aliquot of the centrifuged, diluted sample is added to a solution of enzyme-labeled detection antibody against NGAL in the first tube, into which the dipstick is immersed. Complexes of enzyme-labeled detection antibody with NGAL are bound to the dipstick, which is then washed with tap water and placed in a chromogenic substrate solution in a second tube. The color developed in the substrate solution within a given time is read either by eye and compared with a chart of color intensities which indicates the concentration of NGAL in the urine sample, or in a simple calorimeter that can, for example, be programmed to indicate the NGAL concentration directly.

Example 3

NGAL Lateral Flow Device

A lateral flow device comprised of a strip of porous nitrocellulose or other material with channels capable promoting the migration of liquid by capillary forces is coated near its distal end with a capture antibody against NGAL applied as a transverse band. A further transverse band of antibody against antibodies of the species from which the detection antibody is derived is placed distally to the capture antibody band and serves as a control of strip function. The proximal end of the strip contains the detection antibody against NGAL adsorbed or linked to labeled polystyrene particles or particles of dye complex. When an aliquot of the centrifuged or filtered sample is applied to the proximal end of the strip, the labeled particles attached to detection antibody travel along the strip by capillary attraction. When reaching the band of capture antibody, only those particles which have bound NGAL in the sample will be retained, giving rise to a detectable band. Particles reaching the control band of antibody against the detection antibody will produce a detectable band whether or not any NGAL has been bound. The intensity of the labeled bands can be read by eye in the case of colored particles or by means of the appropriate detection device for the label used. A positive result is indicated by color development or the accumulation of label in both bands, while a negative result is indicated by color development or other label only in the control band. Failure of color development or other label in the control band indicates inadequate strip function. The sensitivity of the test can be regulated by the dilution of the sample applied, which is adjusted so that only NGAL concentrations above the determined cutoff values give rise to a positive result. The sensitivity of the test can also be adjusted by linking the detection antibody to a mixture of labeled and unlabeled particles. Batches of strips can be pre-calibrated and equipped with a calibration code that can be read by the detection device, so that a quantitative or semi-quantitative result can be read from the device. Many variations of the individual aspects of this lateral flow technology are possible, as known to those skilled in the art.

Example 4

NGAL Minicolumn Test

A minicolumn contains a frit made of compressed polyethylene particles allowing the passage of fluid and cells. The frit is coated with capture antibody against human NGAL. The minicolumn is incorporated into a device, which by means of automated liquid handling allows the diluted sample to be applied at a fixed flow rate and volume, followed by detection antibody complexed with dye. After the passage of wash solution, the color intensity of the frit is read by light diffusion photometry. The batches of frits are pre-calibrated and the minicolumns equipped with a calibration code that can be read by the device, so that a quantitative result can be displayed by the instrument without the need for prior calibration with standards.

Example 5

NGAL Sandwich ELISA

Purified recombinant human NGAL for use as a standard and as calibrator material was prepared as described by Kjeldsen et al. (1996). Antibodies against NGAL were those described by Kjeldsen et al. (1993; 1996). Polystyrene ELISA plates were coated overnight at 4° C. with antibody 211-1 at a concentration of 2 µg/mL in 0.05 M sodium carbonate buffer, pH 9.4, applied at 100 µL/well. The wells were emptied, washed 3 times with wash buffer of phosphate-buffered saline, pH 7.4, containing 0.05% Tween 20, and blotted. Dilutions of calibrator and samples in dilution buffer (wash buffer containing bovine albumin at 0.1 mg/mL) were applied to the wells in 100-µL volumes and incubated for 1 hour at room temperature on a shaking table. The wells were then emptied, washed and blotted as before. Biotinylated antibody 211-2 at 0.25 µg/mL in dilution buffer was added to each well at 100 µL/well and incubated for 1 hour at room temperature on a shaking table. The wells were then emptied, washed and blotted as before. A complex of horseradish peroxidase and streptavidin (Zymed, CA) at a dilution of 1/2000 in dilution buffer was added to each well at 100 µL/well and incubated for 1 hour at room temperature on a shaking table. The wells were then emptied, washed and blotted as before. A substrate solution containing tetramethylbenzidine and peroxide (TMB-ONE, Kem-En-Tech, Denmark) was then applied to each well at 100 µL/well and incubated at room temperature in the dark for exactly 8 minutes, after which the color reaction was stopped by adding 50 µL of 1 M sulfuric acid to each well. The light absorbances of the wells at a wavelength of 450 nm were then read in an ELISA plate reader, subtracting the light absorbances at 650 nm. The concentrations of NGAL in the samples were then calculated from the standard curve generated from the light absorbance readings of the calibrators of known concentration.

The assay had a range of 0.02 ng/mL to 1 ng/mL, with a detection limit (95% confidence limit of difference from zero) of 2.4 pg/mL, and showed parallelism between dilutions of purified calibrator and samples.

REFERENCES

Kjeldsen L, Johnsen A H, Sengelov H, Borregaard N (1993) Isolation and primary structure of NGAL, a novel protein associated with human neutrophil gelatinase. J Biol Chem 268:10425-10432.

Kjeldsen L, Koch C, Arnljots K, Borregaard N (1996) Characterization of two ELISAs for NGAL, a newly described lipocalin in human neutrophils. J Immunol Methods 198: 155-164.

Liu Q, Nilsen-Hamilton M (1995) Identification of a new acute phase protein. J Biol Chem 270:22565-22570.

Monier F, Surla A, Guillot M, Morel F (2000) Gelatinase isoforms in urine from bladder cancer patients. Clin Chim Acta 299:11-23.

Stoesz S P, Gould M N (1995) Overexpression of neu-related lipocalin (NRL) in neu-initiated but not ras or chemically initiated rat mammary carcinomas. Oncogene 11:2233-2241.

Triebel S, Blaser J, Reinke H, Tschesche H (1992) A 25 kDa alpha 2-microglobulin-related protein is a component of the 125 kDa form of human gelatinase. FEBS Lett 314: 386-388.

Yan L, Borregaard N, Kjeldsen L, Moses M A (2001) The high molecular weight urinary matrix metalloproteinase (MMP) activity is a complex of gelatinase B/MMP-9 and neutrophil gelatinase-associated lipocalin (NGAL). Modulation of MMP-9 activity by NGAL. J Biol Chem 276:37258-37265.

The invention claimed is:

1. A method of diagnosing the presence of renal injury that has led to acute renal failure or which signifies an immediate risk of developing acute renal failure in a human individual, said method comprising the steps of
    i) determining the concentration of neutrophil gelatinase-associated lipocalin (NGAL) in a sample of urine taken from the individual;
    ii) determining the concentration of NGAL in plasma or serum from a sample of blood taken from the same individual immediately before, during or immediately after the urine sample was collected;
    iii) calculating the ratio of the NGAL concentration in the urine to that in the plasma or serum and comparing the value of the ratio obtained with a cutoff value determined from individuals of the same species without evidence of renal injury,
    iv) diagnosing the presence of the renal injury when the ratio has a value greater than the cutoff value, wherein the cutoff value is a value of at least 0.30 or higher.

2. The method of claim 1, comprising the further step of repeating steps i), ii) and iii) of claim 1 one or more times.

3. The method of claim 1, comprising the further step of repeating steps i), ii) and iii) of claim 1 within 24 hours.

4. The method of claim 1, comprising the further step of repeating steps i), ii) and iii) of claim 1 after a treatment of acute renal failure has been initiated or completed.

5. The method of claim 1, wherein the risk of developing acute renal failure is due to ischemic renal injury.

6. The method of claim 1, wherein the risk of developing acute renal failure is due to a complication of an inflammatory, infective or neoplastic disease.

7. The method of claim 1, wherein the risk of developing acute renal failure is due to critical illness of any cause requiring intensive care.

8. The method of claim 1, wherein the risk of developing acute renal failure is due to a surgical intervention.

9. The method of claim 1, wherein the risk of developing acute renal failure is due to the administration of a nephrotoxic agent.

10. The method of claim 1, wherein NGAL is measured by means of an antibody that binds specifically to human NGAL.

11. The method of claim 1, wherein said cutoff value is a value of at least 0.73 or higher.

12. The method of claim 1, wherein said cutoff value is a value of at least 1.14 or higher.

13. A method of diagnosing the presence of renal injury that has led to acute renal failure or which signifies an immediate risk of developing acute renal failure in a human individual, said method comprising the steps of
   i) determining the concentration of NGAL in a sample of urine taken from the individual;
   ii) determining the concentration of NGAL in plasma or serum from a sample of blood taken from the same individual immediately before, during or immediately after the urine sample was collected;
   iii) calculating the ratio of the NGAL concentration in the plasma or serum to that in the urine and comparing the value of the ratio obtained with a cutoff value determined from individuals of the same species without evidence of renal injury,
   iv) diagnosing the presence of the renal injury when the ratio has a value lower than the cutoff value, wherein the cutoff value is a value of 3.33 or lower.

14. The method of claim 13, comprising the further step of repeating steps i), ii) and iii) of claim 13 one or more times.

15. The method of claim 13, comprising the further step of repeating steps i), ii) and iii) of claim 13 within 24 hours.

16. The method of claim 13, comprising the further step of repeating steps i), ii) and iii) of claim 13 after a treatment of acute renal failure has been initiated or completed.

17. The method of claim 13, wherein the risk of developing acute renal failure is due to ischemic renal injury, a complication of an inflammatory, infective or neoplastic disease, a critical illness of any cause requiring intensive care, a surgical intervention, or the administration of a nephrotoxic agent.

18. The method of claim 13, wherein NGAL is measured by means of an antibody that binds specifically to human NGAL.

19. The method of claim 13, wherein said cutoff value is a value of 1.37 or lower.

20. The method of claim 13, wherein said cutoff value is a value of 0.88 or lower.

* * * * *